US006596892B2

(12) United States Patent
Asai et al.

(10) Patent No.: US 6,596,892 B2
(45) Date of Patent: Jul. 22, 2003

(54) PREPARATION OF LOW MOLECULAR WEIGHT BRANCHED SILOXANES

(75) Inventors: Satoshi Asai, Gunma-ken; Kazumasa Tsukioka, Annaka, both of (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/096,589

(22) Filed: Mar. 14, 2002

(65) Prior Publication Data

US 2002/0133035 A1 Sep. 19, 2002

(30) Foreign Application Priority Data

Mar. 14, 2001 (JP) ........................................ 2001-071788

(51) Int. Cl.[7] .................................................. C07F 7/08
(52) U.S. Cl. ........................ 556/455; 556/451; 556/453
(58) Field of Search .................... 586/451, 453, 586/455

(56) References Cited

U.S. PATENT DOCUMENTS

| 3,549,680 A | 12/1970 | Wegehaupt et al. | |
| 3,839,388 A | 10/1974 | Nitzsche et al. | |
| 4,824,982 A | 4/1989 | Vahlensieck et al. | |
| 5,457,220 A * | 10/1995 | Razzano | 556/453 |
| 5,965,683 A * | 10/1999 | Nye et al. | 556/451 |
| 6,043,388 A * | 3/2000 | Perry | 556/451 |
| 6,232,425 B1 * | 5/2001 | Razzano et al. | 556/453 |

FOREIGN PATENT DOCUMENTS

| DE | 2229514 | 3/1974 |
| EP | 0 435 654 A1 | 7/1991 |
| EP | 0 928 632 A2 | 7/1999 |
| JP | 45-41599 | 12/1970 |
| JP | 11-267508 | 10/1999 |

OTHER PUBLICATIONS

J. Emsley et al., J. Chem. Soc. (A), 1971, pp.2863–2864.
J. Emsley et al., A New and Simple Method of Preparing Dichlorophosphinylphosphorimidic Trichloride, J. Chem. Soc. (A), 1971, pp. 2863–2864, XP–001087957.

* cited by examiner

Primary Examiner—Samuel Barts
(74) Attorney, Agent, or Firm—Birch, Stewart, Kolasch & Birch, LLP

(57) ABSTRACT

A low molecular weight branched siloxane, typically methyltris(trimethylsiloxy)silane is effectively prepared in high yields by reacting a trichlorosilane, typically methyltrichlorosilane with a disiloxane, typically hexamethyldisiloxane in the presence of a linear phosphonitrilic chloride (LPNC) catalyst.

4 Claims, No Drawings

PREPARATION OF LOW MOLECULAR WEIGHT BRANCHED SILOXANES

This invention relates to a method for preparing low molecular weight branched siloxanes, especially methyltris(trimethylsiloxy)silane, useful as industrial siloxane lubricants, cosmetic fluids and cleaning agents.

BACKGROUND OF THE INVENTION

Heretofore, low molecular weight branched siloxanes as represented by the following general formula (3):

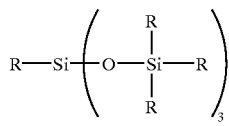
(3)

wherein R is hydrogen or a monovalent hydrocarbon group having 1 to 20 carbon atoms have scarcely been utilized because simple and convenient methods have not been available for their synthesis. This is because, as compared with low molecular weight linear siloxanes, intramolecular branching causes gelation or formation of more by-products during usual equilibration or polymerization reaction. It is very difficult to synthesize a desired low molecular weight branched siloxane in an efficient manner.

SUMMARY OF THE INVENTION

An object of the invention is to provide an efficient method for preparing low molecular weight branched siloxanes of formula (3), especially methyltristrimethylsiloxysilane, in high yields.

It has been found that a low molecular weight branched siloxane of the general formula (3) is efficiently prepared by reacting a trichlorosilane of the general formula (1) with a disiloxane of the general formula (2) in the presence of a linear phosphonitrilic chloride (LPNC) catalyst.

 RSiCl$_3$ (1)

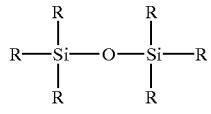
(2)

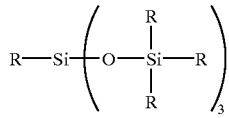
(3)

Herein R is hydrogen or a monovalent hydrocarbon group having 1 to 20 carbon atoms.

DESCRIPTION OF THE PREFERRED EMBODIMENT

According to the invention, a low molecular weight branched siloxane is efficiently prepared by reacting a trichlorosilane with a disiloxane in the presence of a LPNC catalyst.

The trichlorosilane and disiloxane used herein as the starting reactants have the general formulae (1) and (2), respectively.

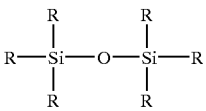
(2)

Herein, R is hydrogen or a monovalent hydrocarbon group having 1 to 20 carbon atoms, examples of which include alkyl groups such as methyl, ethyl, propyl, butyl, pentyl, hexyl, heptyl, octyl, dodecyl and octadecyl, cycloalkyl groups such as cyclohexyl, alkenyl groups such as vinyl and allyl, aryl groups such as phenyl and tolyl, aralkyl groups such as benzyl, and substituted groups in which some or all of the hydrogen atoms on the foregoing groups are substituted with fluorine. A plurality of R's may be identical or different. Of these, methyl is most preferred for ease of reaction.

Methyltrichlorosilane is most preferred among the trichlorosilanes of formula (1), and hexamethyldisiloxane is most preferred among the disiloxanes of formula (2).

The trichlorosilane and disiloxane are preferably used in a molar ratio between 1:1 and 1:9. To increase the amount of a desired low molecular weight branched siloxane formed and suppress the formation of by-products, use of the disiloxane in excess relative to the trichlorosilane on a molar basis is recommended. Most preferably, the trichlorosilane and disiloxane are used in a molar ratio of 1:4.5.

The low molecular weight branched siloxane produced by reacting the trichlorosilane of formula (1) with the disiloxane of formula (2) in the presence of a LPNC catalyst has the general formula (3) wherein R is as defined above.

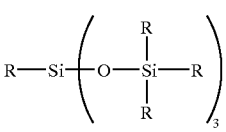
(3)

Particularly when methyltrichlorosilane as the trichlorosilane of formula (1) and hexamethyldisiloxane as the disiloxane of formula (2) are reacted in a molar ratio in the above range in the presence of a LPNC catalyst, a low molecular weight branched siloxane of the following general formula (4) is obtainable in high yields in the form of a reaction solution which is easy to purify by distillation in the subsequent step and contains less by-products.

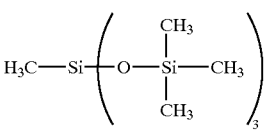
(4)

Especially when methyltrichlorosilane and hexamethyldisiloxane are reacted in a molar ratio between 1:1 and 1:9, desirably 1:4 and 1:6, in the presence of a LPNC catalyst, methyltris(trimethylsiloxy)silane is selectively synthesized.

The catalyst used herein is a linear phosphonitrilic chloride (LPNC) catalyst. The synthesis of this catalyst is known in the art as disclosed in J. Emsley et al., J. Chem. Soc. A (1971) 2863. See also U.S. Pat. No. 3,839,388, German Patent OS 2229514, JP-A 11-267508 and many other patent publications. The reaction promoting ability of a particular LPNC catalyst largely depends on the amounts of phosphorus and nitrogen used in the synthesis of that catalyst. Preferably, the molar ratio of phosphorus to nitrogen is from 1:1 to 4:1, more preferably from 2:1 to 3:1.

It is noted that most commercially available cyclic phosphonitrilic chlorides (CPNCs) are little active.

It is also noted that in JP-B 45-41599, organic silicon halide compounds are synthesized by carrying out substitution reaction, similar to the present reaction, in the presence of a LPNC catalyst. This patent, however, fails to efficiently synthesize low molecular weight branched siloxanes desired in the present invention and does not refer to the activity of LPNC catalyst used.

The LPNC catalyst is used in a catalytic amount. Too small an amount of the LPNC catalyst may retard the reaction whereas with too large an amount, the reaction may become too fast to control. Then the LPNC catalyst is preferably used in an amount of 0.01 to 1%, and more preferably 0.05 to 0.2% by weight based on the starting silane and siloxane combined.

The reaction temperature is preferably set in the range of 0° C. to 100° C. At temperatures below 0° C., the reaction rate may become so slow that a long time is taken until the completion of reaction. The preferred temperature is from 15° C. to 30° C. In this case, the reaction time is about 1 to 6 hours.

After the completion of reaction, the end low molecular weight branched siloxanes are collected by conventional distillation of the reaction solution. If necessary, the LPNC catalyst is deactivated by any well-known technique, with better results being obtained.

EXAMPLE

Examples of the invention are given below by way of illustration and not by way of limitation.

It is noted that the. LPNC catalyst used herein was synthesized according to Example of JP-A 11-267508. It was prepared by blending 8.66 g of phosphorus pentachloride, 2.23 g of hexamethyldisilazane and 200 g of hexamethyldisiloxane, the molar ratio of phosphorus to nitrogen being 3:1.

Example 1

A 500-ml separable flask was charged with a solution mixture of 229.6 g of hexamethyldisiloxane and 70.4 g of methyltrichlorosilane (molar ratio 3:1). With stirring at 25° C., 9 g of the LPNC catalyst prepared above was added and reaction effected for 6 hours. Purification by conventional distillation gave 52.9 g (yield 36.2%) of methyltris(trimethylsiloxy)silane. By NMR, IR and other analysis, the structure of the isolated product was confirmed. (The same applies to the following Examples.)

Comparative Example 1

A 500-ml separable flask was charged with a solution mixture of 229.6 g of hexamethyldisiloxane and 70.4 g of methyltrichlorosilane (molar ratio 3:1). With stirring at 25° C., 0.15 g of a CPNC catalyst was added. Even after 6 hours of reaction, no methyltris(trimethylsiloxy)silane was produced.

Example 2

A 500-ml separable flask was charged with a solution mixture of 249.1 g of hexamethyldisiloxane and 50.9 g of methyltrichlorosilane (molar ratio 4.5:1). With stirring at 25° C., 9 g of the LPNC catalyst prepared above was added and reaction effected for 2 hours. Purification by conventional distillation gave 74.8 g (yield 70.8%) of methyltristrimethylsiloxysilane.

Example 3

A 500-ml separable flask was charged with a solution mixture of 241.4 g of hexamethyldisiloxane and 58.6 g of propyltrichlorosilane (molar ratio 4.5:1). With stirring at 25° C., 9 g of the LPNC catalyst prepared above was added and reaction effected for 3 hours. Purification by conventional distillation gave 76.5 g (yield 68.5%) of propyltristrimethylsiloxysilane.

There has been described an efficient method for preparing low molecular weight branched siloxanes, especially methyltris(trimethylsiloxy)silane, in high yields.

Japanese Patent Application No. 2001-071788 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for preparing a low molecular weight branched siloxane of the general formula (3) shown below, comprising the step of reacting a trichlorosilane of the general formula (1) shown below with a disiloxane of the general formula (2) shown below in the presence of a linear phosphonitrilic chloride (LPNC) catalyst,

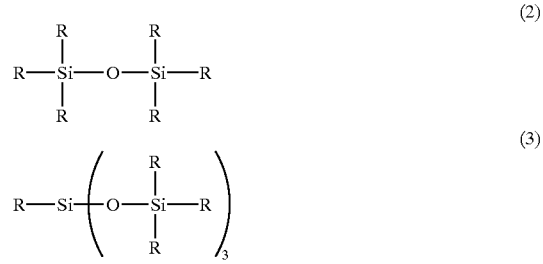

wherein R is hydrogen or a monovalent hydrocarbon group having 1 to 20 carbon atoms.

2. The method of claim 1 wherein the LPNC catalyst has a molar ratio of phosphorus to nitrogen from 1:1 to 4:1.

3. A method for preparing a methyltris(trimethylsiloxy)silane of the general formula (4):

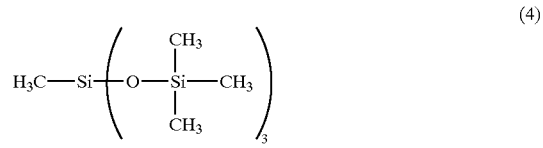

said method comprising the step of reacting methyltrichlorosilane with hexamethyldisiloxane in the presence of a linear phosphonitrilic chloride (LPNC) catalyst.

4. The method of claim 3 wherein methyltrichlorosilane and hexamethyldisiloxane are used in a molar ratio of from 1:1 to 1:9.

* * * * *